(12) United States Patent
Mohr et al.

(10) Patent No.: US 8,892,224 B2
(45) Date of Patent: Nov. 18, 2014

(54) METHOD FOR GRAPHICALLY PROVIDING CONTINUOUS CHANGE OF STATE DIRECTIONS TO A USER OF A MEDICAL ROBOTIC SYSTEM

(71) Applicant: Intuitive Surgical Operations, Inc., Sunnyvale, CA (US)

(72) Inventors: Paul W. Mohr, Mountain View, CA (US); David W. Robinson, Mountain View, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 0 days.

(21) Appl. No.: 14/052,835

(22) Filed: Oct. 14, 2013

(65) Prior Publication Data

US 2014/0039521 A1     Feb. 6, 2014

Related U.S. Application Data

(63) Continuation of application No. 13/654,631, filed on Oct. 18, 2012, now Pat. No. 8,583,274, which is a continuation of application No. 12/238,631, filed on Sep. 26, 2008, now Pat. No. 8,315,720.

(51) Int. Cl.
    *A61B 19/00*         (2006.01)
    *B25J 9/16*          (2006.01)

(52) U.S. Cl.
    CPC ..... *A61B 19/5225* (2013.01); *A61B 2019/4857* (2013.01); *A61B 19/2203* (2013.01);

(Continued)

(58) Field of Classification Search
    CPC ............... A61B 19/2203; A61B 19/56; A61B 19/5244; A61B 2017/00017; A61B 2017/00022; A61B 2017/00075; A61B 2017/00115; A61B 2017/00128; A61B 2017/00212; A61B 2017/00225; A61B 2017/00234; A61B 2017/00367; A61B 2017/0019
    USPC ............... 700/257, 264, 249, 245, 3, 83, 180, 700/184, 28, 32, 33; 715/3, 83, 180, 184, 715/705; 901/2, 6, 9, 50
    See application file for complete search history.

(56) References Cited

U.S. PATENT DOCUMENTS 5,221,283 A     6/1993    Chang
5,251,127 A    10/1993    Raab (Continued)

FOREIGN PATENT DOCUMENTS

EP            1650615 A1    4/2006
WO    WO-2007017642 A1    2/2007

OTHER PUBLICATIONS

Majdani et al., Volume Computed Tomography for navigated procedures at the lateral skull base—proof of feasibility on phantom and human temporal bone specimens, 2007, GMS CURAC.*

(Continued)

*Primary Examiner* — Thomas G Black
*Assistant Examiner* — Sara Nelson

(57) ABSTRACT

Continuous change of state directions are graphically provided on a display screen to assist a user in performing necessary action(s) for transitioning between operating modes in a medical robotic system or performing corrective action. A graphical representation of a target state of an element of the medical robotic system is displayed on a display screen viewable by the user. Current states of the element and indications directing the user to manipulate the element towards the target state are continuously determined and graphical representations of the continuously determined current states and indications are displayed on the display screen along with that of the target state.

10 Claims, 6 Drawing Sheets

(52) U.S. Cl.
CPC ..... *G05B 2219/45123* (2013.01); *B25J 9/1692* (2013.01); *B25J 9/1689* (2013.01); *G05B 2219/39024* (2013.01); *A61B 2019/2223* (2013.01); *A61B 19/56* (2013.01); *Y10S 901/02* (2013.01); *Y10S 901/06* (2013.01); *Y10S 901/09* (2013.01)
USPC ............ 700/83; 700/257; 700/264; 700/3; 715/700; 715/705; 901/2; 901/6; 901/9

(56) References Cited

U.S. PATENT DOCUMENTS

| | | | |
|---|---|---|---|
| 5,553,198 | A | 9/1996 | Wang et al. |
| 5,769,092 | A | 6/1998 | Williamson, Jr. |
| 6,645,196 | B1 | 11/2003 | Nixon et al. |
| 6,766,204 | B2 | 7/2004 | Niemeyer et al. |
| 6,799,065 | B1 * | 9/2004 | Niemeyer ............... 600/407 |
| 6,856,324 | B2 | 2/2005 | Sauer et al. |
| 7,236,618 | B1 * | 6/2007 | Chui et al. ............... 382/128 |
| 7,386,365 | B2 | 6/2008 | Nixon |
| 7,524,320 | B2 | 4/2009 | Tierney et al. |
| 7,599,730 | B2 * | 10/2009 | Hunter et al. ........... 600/424 |
| 7,809,176 | B2 * | 10/2010 | Gundel ................... 382/128 |
| 8,004,229 | B2 | 8/2011 | Nowlin et al. |
| 8,315,720 | B2 | 11/2012 | Mohr et al. |
| 8,583,274 | B2 | 11/2013 | Mohr et al. |
| 2003/0208122 | A1 | 11/2003 | Melkent et al. |
| 2004/0034302 | A1 | 2/2004 | Abovitz et al. |
| 2005/0107808 | A1 * | 5/2005 | Evans et al. ............ 606/139 |
| 2005/0148855 | A1 * | 7/2005 | Kienzle, III ............ 600/407 |
| 2005/0203380 | A1 | 9/2005 | Sauer et al. |
| 2006/0004286 | A1 * | 1/2006 | Chang et al. ........... 600/435 |
| 2007/0021738 | A1 | 1/2007 | Hasser et al. |
| 2007/0049435 | A1 | 3/2007 | Jinno et al. |
| 2007/0142825 | A1 | 6/2007 | Prisco et al. |
| 2007/0197896 | A1 * | 8/2007 | Moll et al. ............... 600/407 |
| 2007/0287992 | A1 | 12/2007 | Diolaiti et al. |
| 2008/0033240 | A1 | 2/2008 | Hoffman et al. |
| 2009/0062813 | A1 | 3/2009 | Prisco et al. |
| 2009/0192523 | A1 | 7/2009 | Larkin et al. |
| 2010/0161129 | A1 | 6/2010 | Costa et al. |
| 2010/0174410 | A1 * | 7/2010 | Greer et al. ............. 700/264 |
| 2010/0234857 | A1 | 9/2010 | Itkowitz et al. |
| 2010/0274087 | A1 * | 10/2010 | Diolaiti et al. .......... 600/118 |
| 2011/0166706 | A1 | 7/2011 | Prisco et al. |
| 2012/0109377 | A1 * | 5/2012 | Stern et al. .............. 700/259 |
| 2013/0085382 | A1 * | 4/2013 | Ramamurthy et al. ... 600/424 |
| 2013/0253524 | A1 * | 9/2013 | Amis et al. ............... 606/96 |
| 2014/0039298 | A1 * | 2/2014 | Whitcomb et al. ..... 600/414 |

OTHER PUBLICATIONS

PCT/US09/55695 International Search Report and Written Opinion of the International Searching Authority, mailed Nov. 18, 2009, 14 pages.

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

* cited by examiner

METHOD FOR GRAPHICALLY PROVIDING CONTINUOUS CHANGE OF STATE DIRECTIONS TO A USER OF A MEDICAL ROBOTIC SYSTEM

CROSS REFERENCE TO RELATED APPLICATIONS

This application is a continuation of application Ser. No. 13/654,631, filed Oct. 18, 2012, now U.S. Pat. No. 8,583,274, which is a continuation of application Ser. No. 12/238,631, filed Sep. 26, 2008, now U.S. Pat. No. 8,315,720, each of which is incorporated herein by reference.

FIELD OF THE INVENTION

The present invention generally relates to medical robotic systems and in particular, to a method for graphically providing continuous change of state directions to a user of a medical robotic system.

BACKGROUND OF THE INVENTION

Medical robotic systems such as those used in performing minimally invasive surgical procedures offer many benefits over traditional open surgery techniques, including less pain, shorter hospital stays, quicker return to normal activities, minimal scarring, reduced recovery time, and less injury to tissue. Consequently, demand for minimally invasive surgery using such medical robotic systems is strong and growing.

Examples of medical robotic systems include the da Vinci® Surgical System and the da Vinci® S™ Surgical System from Intuitive Surgical, Inc., of Sunnyvale, Calif. Each of these systems includes a surgeon's console, a patient-side cart, a high performance three-dimensional ("3-D") vision system, and Intuitive Surgical's proprietary EndoWrist® articulating instruments, which are modeled after the human wrist so that when added to the motions of manipulators holding the surgical instruments, they allow at least six degrees of freedom of motion, which is comparable to or even greater than the natural motions of open surgery.

The da Vinci® surgeon's console has a high-resolution stereoscopic video display with two progressive scan cathode ray tubes ("CRTs"). The system offers higher fidelity than polarization, shutter eyeglass, or other techniques. Each eye views a separate CRT presenting the left or right eye perspective, through an objective lens and a series of mirrors. The surgeon sits comfortably and looks into this display throughout surgery, making it an ideal place for the surgeon to display and manipulate 3-D intraoperative imagery.

The patient-side cart typically includes three or more robotic arm assemblies with corresponding slave manipulators for holding and manipulating medical devices such as surgical instruments (or other tools) and image capturing devices for performing and/or viewing a medical procedure at a surgical site within a patient. To manipulate these medical devices, the surgeon's console also includes input devices which may be selectively associated with the medical devices and their respective slave manipulators. Since the movements of the input devices and their associated medical devices are scaled, this allows the surgeon to perform intricate medical procedures with greater ease than conventional open surgery as an operator of the medical robotic system. Further, it may even allow the surgeon to perform medical procedures that are not even feasible using conventional open surgery techniques.

To perform a minimally invasive surgical procedure on a patient, one or more incisions are first made in the patient and cannulae inserted therein to gain access to a surgical site within the patient. Setup arms supporting the slave manipulators are then positioned so as to allow the slave manipulators to attach to respective of the cannulae. Surgical instruments engaged on the slave manipulators are then inserted into the cannulae and properly positioned and oriented in order to perform the procedure. A surgeon may then manipulate input devices which are coupled to the slave manipulators and their respective surgical instruments through one or more controllers to perform the surgical procedure.

Numerous operational modes may be implemented in a medical robotic system and transitions between such operational modes may be governed by sophisticated state machines. When a user wants to effect a change of mode in the system, he or she may be required to perform one or more steps to satisfy the relevant mode-change criteria demanded by the state machine. When the criteria are purely discrete, they may be described simply with a static icon or dialog box message (e.g., "Press Fault Recover to Continue"). However, in some medical robotic systems, the mode-change criteria may require the user to manipulate one or more input devices continuously and in a certain fashion until the actions required to complete the mode change are successfully performed. In such systems, it may be difficult for the user to understand what he or she must do to effect the mode change if only a simple static icon or discrete message is provided—thus, making the system more difficult to use and harder to learn.

OBJECTS AND SUMMARY OF THE INVENTION

Accordingly, one object of one or more aspects of the present invention is a medical robotic system that conveys to its user the necessary actions required to be performed by the user to effect a mode change or take corrective action in the system.

Another object of one or more aspects of the present invention is a medical robotic system that is simple to use, easy to learn, and safe to operate.

These and additional objects are accomplished by the various aspects of the present invention, wherein briefly stated, one aspect is a method for graphically providing continuous change of state directions to a user of a medical robotic system, the method comprising: displaying a graphical representation of a target state of an element of the medical robotic system on a display screen viewable by the user; continuously determining current states of the element and indications directing the user to manipulate the element towards the target state; and displaying graphical representations of the current states of the element and the indications along with the target state on the display screen.

Another aspect is a medical robotic system comprising: an element; a display screen; and a processor programmed to graphically provide continuous change of state directions to a user of the medical robotic system by displaying a graphical representation of a target state of the element on the display screen, continuously determining current states of the element along with indications directing the user to manipulate the element towards the target state, and displaying graphical representations of the current states of the element and the indications along with the target state on the display screen.

Additional objects, features and advantages of the various aspects of the present invention will become apparent from the following description of its preferred embodiment, which description should be taken in conjunction with the accompanying drawings.

DETAILED DESCRIPTION OF THE PREFERRED EMBODIMENT

Figure 1:
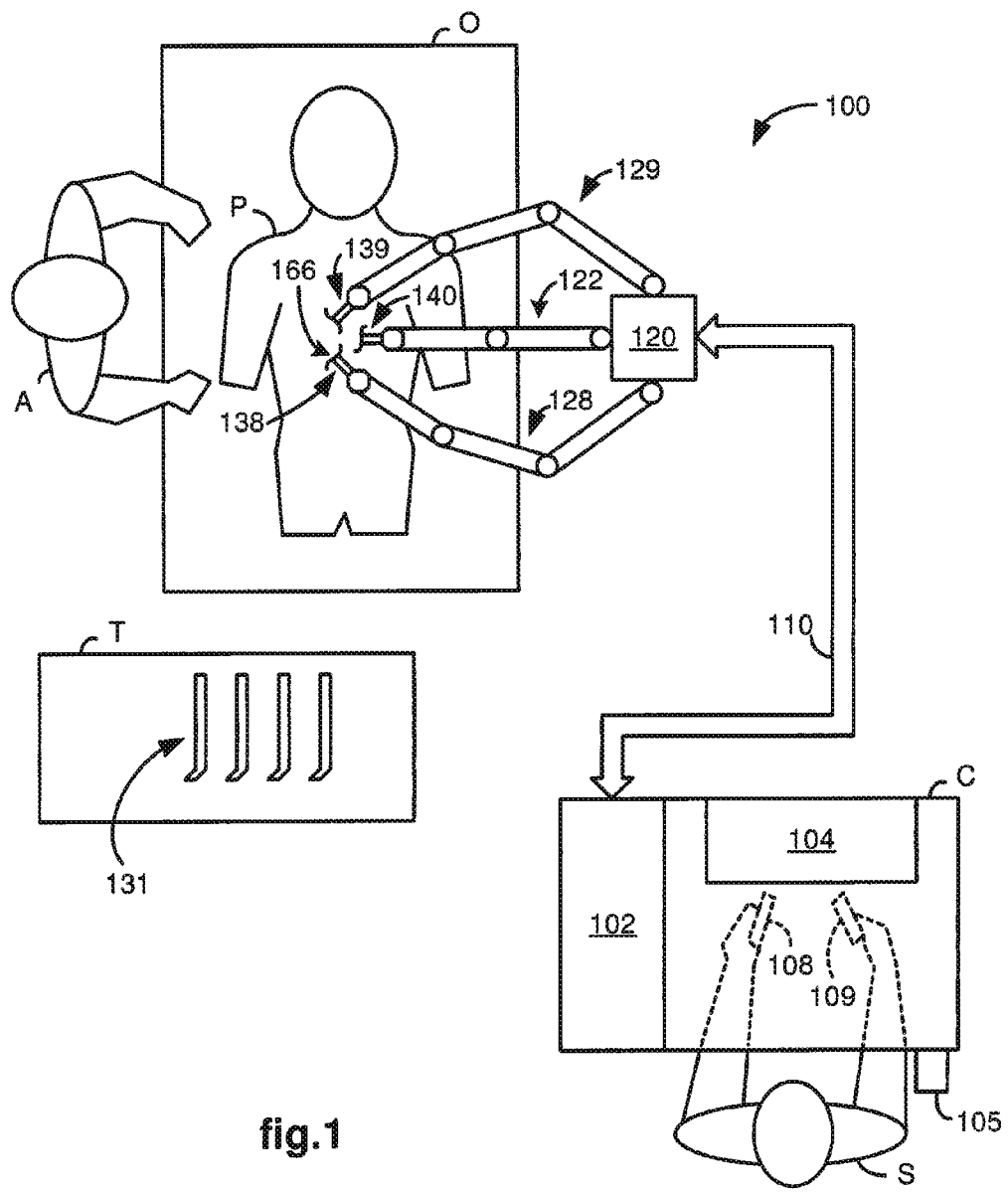
FIG. 1 illustrates a top view of an operating room employing a medical robotic system utilizing aspects of the present invention.

FIG. 1 illustrates, as an example, a top view of an operating room employing a medical robotic system. The medical robotic system in this case is a minimally invasive robotic surgical system 100 including a Console ("C") utilized by a Surgeon ("S") while performing a medical procedure, such as a diagnostic or surgical procedure, with assistance from one or more Assistants ("A"), on a Patient ("P") who is reclining on an Operating table ("O").

The Console includes a 3-D monitor 104 for displaying a 3-D image of a surgical site to the Surgeon, left and right manipulatable input devices 108, 109, a foot pedal 105, and a processor 102. The input devices 108, 109 may include any one or more of a variety of input devices such as joysticks, gloves, trigger-guns, hand-operated controllers, or the like. The processor 102 may be a dedicated computer integrated into the Console or positioned next or near to it, or it may be broken up into a number of processing or controller components that are distributed in a distributed processing fashion throughout the system 100.

The Surgeon performs a medical procedure by manipulating the input devices 108, 109 (also referred to herein as "master manipulators") so that the processor 102 causes slave manipulators of their respectively associated robotic arm assemblies 128, 129 to manipulate their respective removably coupled surgical instruments 138, 139 (also referred to herein as "tools") accordingly, while the Surgeon views the surgical site in 3-D on the Console monitor 104 as it is captured by a stereoscopic endoscope 140. To properly position the endoscope 140, one or both of the input devices 108, 109 may be temporarily associated with the endoscope 140 (as described in reference to FIG. 4) so that when the Surgeon manipulates the input device(s), the processor 102 causes a slave manipulator of the robotic arm assembly 122 to move the endoscope 140 accordingly. The robotic arm assemblies 128, 129, 122 are mounted on a mobile Patient side cart 120 and communicate through electronics on the cart 120 with the processor 102 through bus 110.

Each of the tools 138, 139, as well as the Endoscope 140, is conventionally inserted through a tool guide or cannula (not shown) into the Patient so as to extend down to the surgical site through a corresponding minimally invasive incision such as Incision 166. The number of surgical tools used at one time and consequently, the number of robotic arms being used in the system 100 will generally depend on the medical procedure being performed and the space constraints within the operating room, among other factors. If it is necessary to change a tool being used during a procedure, the Assistant may remove the tool no longer being used from its robotic arm assembly, and replace it with another tool 131 from a Tray ("T") in the operating room. A guided tool change procedure may then be performed as described, for example, in U.S. Pat. No. 6,645,196 entitled "Guided Tool Change," which is incorporated herein by reference.

Each of the robotic arm assemblies 122, 128, 129 includes a slave manipulator and setup arms. The slave manipulators are robotically moved using motor controlled joints (also referred to herein as "active joints") in order to manipulate and/or move their respectively held medical devices. The setup arms may be manually manipulated by releasing normally braked joints (also referred to herein as "setup joints") to horizontally and vertically position the robotic arm assemblies 122, 128, 129 so that their respective medical devices may be inserted into their respective tool guides.

Preferably, the monitor 104 is positioned near the Surgeon's hands so that it will display a projected image that is oriented so that the Surgeon feels that he or she is actually looking directly down onto the operating site. To that end, images of the tools 138, 139 preferably appear to be located substantially where the Surgeon's hands are located.

The processor 102 performs various functions in the system 100. One important function that it performs is to translate and transfer the mechanical motion of input devices 108, 109 to their respective slave manipulators of robotic arm assemblies 128, 129 (in tool following mode) by generating and transmitting digital control signals over bus 110 so that the Surgeon can effectively manipulate their respective tools 138, 139. Another important function is to implement various controllers such as those described in reference to FIG. 4 and the method described in reference to FIG. 5.

Although described as a processor, it is to be appreciated that the processor 102 may be implemented in practice by any combination of hardware, software and firmware. Also, its functions as described herein may be performed by one unit, or divided up among different components, each of which may be implemented in turn by any combination of hardware, software and firmware, and distributed, in a distributed processing fashion, about the system 100.

For additional details on the construction and operation of medical robotic systems such as described herein, see, e.g., U.S. Pat. No. 6,493,608 "Aspects of a Control System of a Minimally Invasive Surgical Apparatus," and U.S. Pat. No. 6,424,885 "Camera Referenced Control in a Minimally Invasive Surgical Apparatus," which are incorporated herein by reference.

Figure 2:
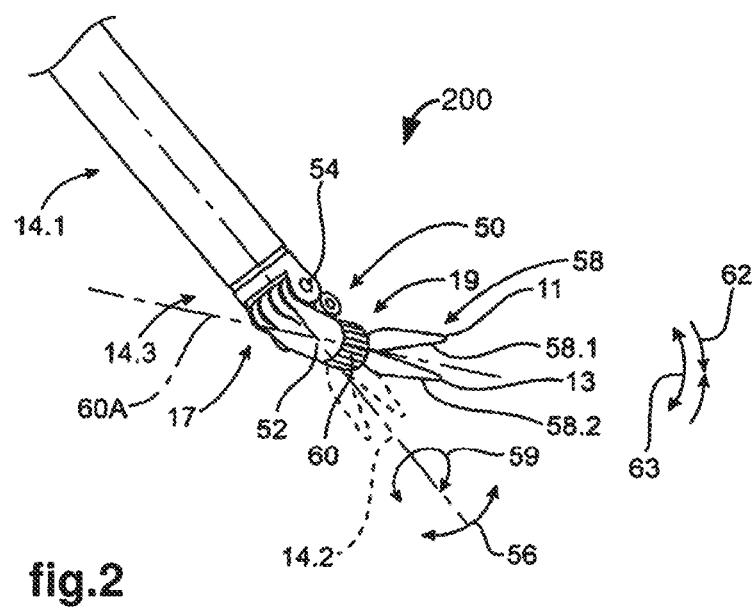
FIG. 2 illustrates a perspective view of an end effector of a medical device used in a medical robotic system utilizing aspects of the present invention.

FIG. 2 illustrates, as an example, a perspective view of a distal end of a medical device 200, such as one of the surgical tools 138, 139, which is mechanically coupled through an interface (not shown) to a slave manipulator of a robotic arm assembly. The medical device 200 has a shaft 14.1 which is coupled at its proximal end to the interface and coupled at its distal end 14.3 to a wrist-like mechanism 50. The medical device 200 further has an end effector 58 which is coupled to the wrist-like mechanism 50.

The wrist-like mechanism 50 includes a wrist member 52. One end portion of the wrist member 52 is pivotally mounted in a clevis 17 by means of a pivotal connection 54 so that the wrist member 52 can pivot in the direction of arrows 56 about the pivotal connection 54. The end effector 58 is pivotally mounted on an opposed end of the wrist member 52. The end effector 58 is in the form of, e.g., a clip applier for anchoring clips during a surgical procedure. Accordingly, the end effector 58 has two parts 58.1, 58.2 together defining a jaw-like arrangement. It will be appreciated that the end effector 58 can be in the form of any required surgical tool having two members or fingers which pivot relative to each other, such as scissors, pliers for use as needle drivers, or the like. Alternatively, it may include a single working member, e.g., a scalpel, cautery electrode, or the like. When a tool other than a clip applier is required during the surgical procedure, the medical device 200 may be simply removed from its associated robotic arm assembly and replaced with another surgical tool, such as tool 131 in FIG. 1, bearing the required end effector, e.g., a scissors, or pliers, or the like.

The end effector 58 is pivotally mounted in a clevis 19, on an opposed end of the wrist member 52, by means of a pivotal connection 60. Free ends 11, 13 of the parts 58.1, 58.2 are angularly displaceable about the pivotal connection 60 toward and away from each other as indicated by arrows 62, 63. Members 58.1, 58.2 can be displaced angularly about the pivotal connection 60 to change the orientation of the end effector 58 as a whole, relative to the wrist member 52. Thus, each part 58.1, 58.2 is angularly displaceable about the pivotal connection 60 independently of the other, so that the end effector 58, as a whole, is angularly displaceable about the pivotal connection 60 as indicated in dashed lines in FIG. 2. Furthermore, the shaft 14.1 is rotatable about its central axis 14.2 as indicated by the arrows 59. Thus, the end effector 58 has three orientational degrees of freedom of movement relative to the working end 14.3, namely, rotation about the axis 14.2 as indicated by arrows 59, angular displacement as a whole about the pivot 60 and angular displacement about the pivot 54 as indicated by arrows 56. The orientational movement of the end effector 58 is controlled by appropriately positioned actuators (e.g., electrical motors) in its coupled to robotic arm assembly, which respond to inputs from its associated input device through the processor 102 to drive the end effector 58 to a desired orientation as dictated by movement of the input device.

Figure 3:
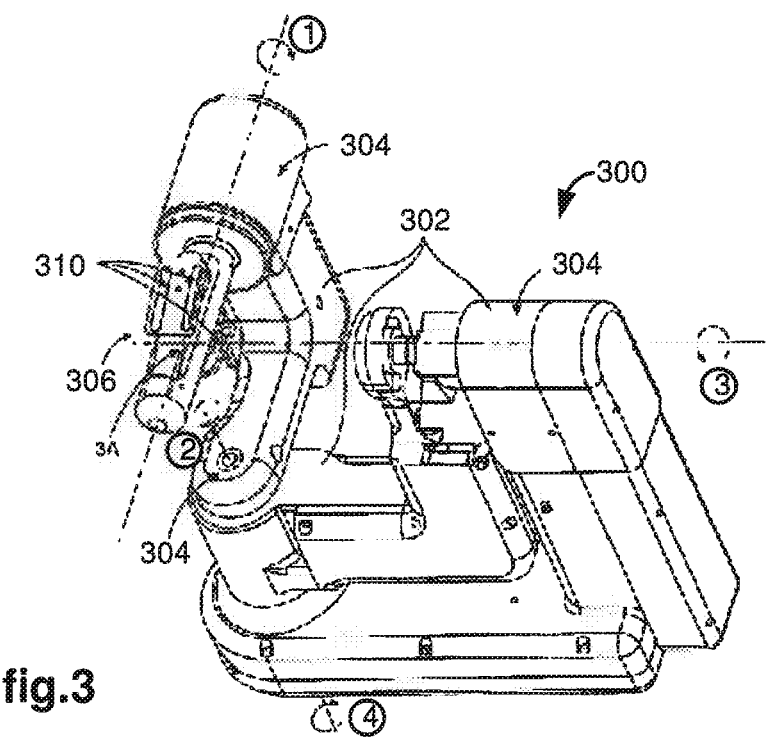
FIG. 3 illustrates a perspective view of parts of an input device used in a medical robotic system utilizing aspects of the present invention.

FIG. 3 illustrates, as an example, a perspective view of a hand-held or hand-grippable part 300 of the input device (e.g., 108 or 109) associated with the medical device 200. The part 300 has an articulated arm portion including a plurality of members or links 302 connected together by joints 304. The Surgeon grips the part 300 by positioning his or her thumb and index finger over a pincher formation 306. The joints of the part 300 are operatively connected to electric motors to provide for, e.g., force feedback, gravity compensation, and/or the like. Appropriately positioned sensors, e.g., encoders, or potentiometers, or the like, are positioned on each joint of the part 300, so as to enable the joint positions to be determined for commanding movement of the medical device 200 through a control system implemented in the processor 102 to drive its associated slave manipulator.

As shown in FIG. 3, the part 300 has a plurality of degrees of freedom movement. First of all, the part 300 is mountable on another part of the input device that facilitates translational movement of the part 300. Secondly, the pincher formation 306 of the part 300 is rotatable about several axes shown as dotted lines in FIG. 3. In particular, the pincher formation 306 may be rotated in a direction 1 so as to command the end effector 58 to rotate about the axis 14.2 as indicated by arrows 59, the pincher formation 306 may be rotated in a direction 2 to command the end effector 58 to rotate about the pivot 60, and the pincher formation 306 may be rotated in a direction 3 to command the end effector 58 to rotate about the pivot 54 as indicated by arrows 56.

Further, when the pincher formation 306 of the hand-grippable part 300 is squeezed between the thumb and index finger of the Surgeon, the fingers 58.1, 58.2 of the end effector 58 close. When the thumb and index finger of the Surgeon cause the pincher formation 306 to be moved apart, the fingers 58.1, 58.2 of the end effector 58 move apart in sympathy.

Figure 4:
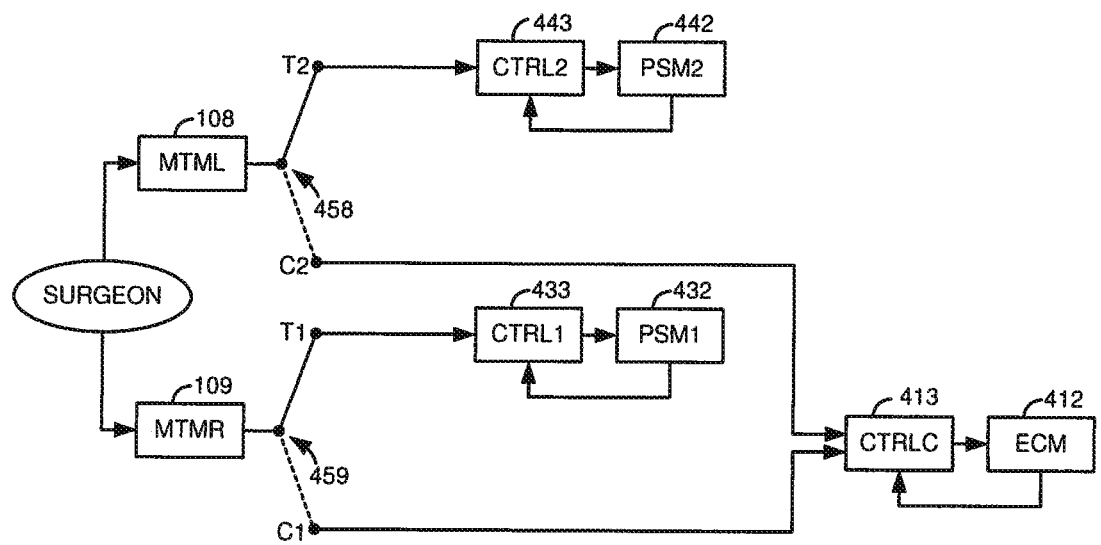
FIG. 4 illustrates a block diagram of components for controlling and selectively associating device manipulators to left and right hand-manipulatable input devices in a medical robotic system utilizing aspects of the present invention.

FIG. 4 illustrates, as an example, a block diagram of components for controlling and selectively associating device manipulators to the input devices 108, 109. Various surgical tools such as graspers, cutters, and needles may be used to perform a medical procedure at a work site within the Patient. In this example, two surgical tools 138, 139 are used to robotically perform the procedure and the camera 140 is used to view the procedure. The tools 138, 139 and camera 140 are inserted through their respective ports into the Patient using the setup portion of their respective robotic arm assemblies 128, 129, 122 and maneuvered by slave manipulators of their respective robotic arm assemblies 128, 129, 122 towards the work site where the medical procedure is to be performed.

Each of the devices 138, 139, 140 is manipulated by its own slave manipulator. In particular, the camera 140 is manipulated by a camera manipulator (ECM) 412, the first surgical tool 139 is manipulated by a first tool manipulator (PSM1) 432, and the second surgical tool 138 is manipulated by a second tool manipulator (PSM2) 442. So as to not overly encumber the figure, the devices 138, 139, 140 are not shown, only their respective manipulators 442, 432, 412 are shown in the figure.

In this example, each of the input devices 108, 109 may be selectively associated with one of the devices 138, 139, 140 so that the associated device may be controlled by the input device through its controller and manipulator. For example, by placing switches 458, 459 respectively in tool following modes "T2" and "T1", the left and right input devices 108, 109 may be respectively associated with the second and first surgical tools 138, 139, which are telerobotically controlled through their respective controllers 443, 433 and manipulators 442, 432 so that the Surgeon may perform a medical procedure on the Patient while the camera 140 is soft-locked in place by its controller 413.

When the camera 140 is to be repositioned by the Surgeon, either one or both of the left and right input devices 108, 109 may be associated with the camera 140 so that the Surgeon may move the camera 140 through its controller 413 and manipulator 412. In this case, the disassociated one(s) of the surgical tools 138, 139 is soft-locked in place by its controller. For example, by placing switches 458, 459 respectively in camera positioning modes "C2" and "C1", the left and right input devices 108, 109 may be associated with the camera 140, which is telerobotically controlled through its controller 413 and manipulator 412 so that the Surgeon may position the camera 140 while the surgical tools 138, 139 are soft-locked in place. If only one input device is to be used for positioning the camera, then only one of the switches 458, 459 is placed in its camera positioning mode while the other one of the switches 458, 459 remains in its tool following mode so that its respective input device may continue to control its associated surgical tool.

The selective association of the input devices 108, 109 to other devices in this example may be performed by the Surgeon using a Graphical User Interface (GUI) or a voice recognition system implemented on the Surgeon Console. Alternatively, the association of the input devices 108, 109 may be changed by the Surgeon depressing a button on one of the input devices 108, 109, depressing the foot pedal 105, or using any other well known mode switching technique.

After the Surgeon has temporarily associated the input devices 108, 109 with the camera 140 and moved the camera 140 to its desired position and/or orientation to gain a better view of a worksite, the Surgeon must then re-associate the input devices 108, 109 with their formerly associated surgical tools 138, 139 before performing a medical procedure at the worksite. In order to avoid abrupt movement of the surgical tools 138, 139 due to their respective controllers 443, 433 correcting for their misalignment with the input devices 108, 109, it is desirable to re-align the input devices 108, 109 with the surgical tools 138, 139 before effecting the re-association. The steps necessary to re-align the input devices 108, 109 with the soft-locked surgical tools 138, 139 may not be readily known by the Surgeon, however. Therefore, it would be desirable for the medical robotic system 100 to provide guidance to the Surgeon to perform the re-alignment.

Figure 5:
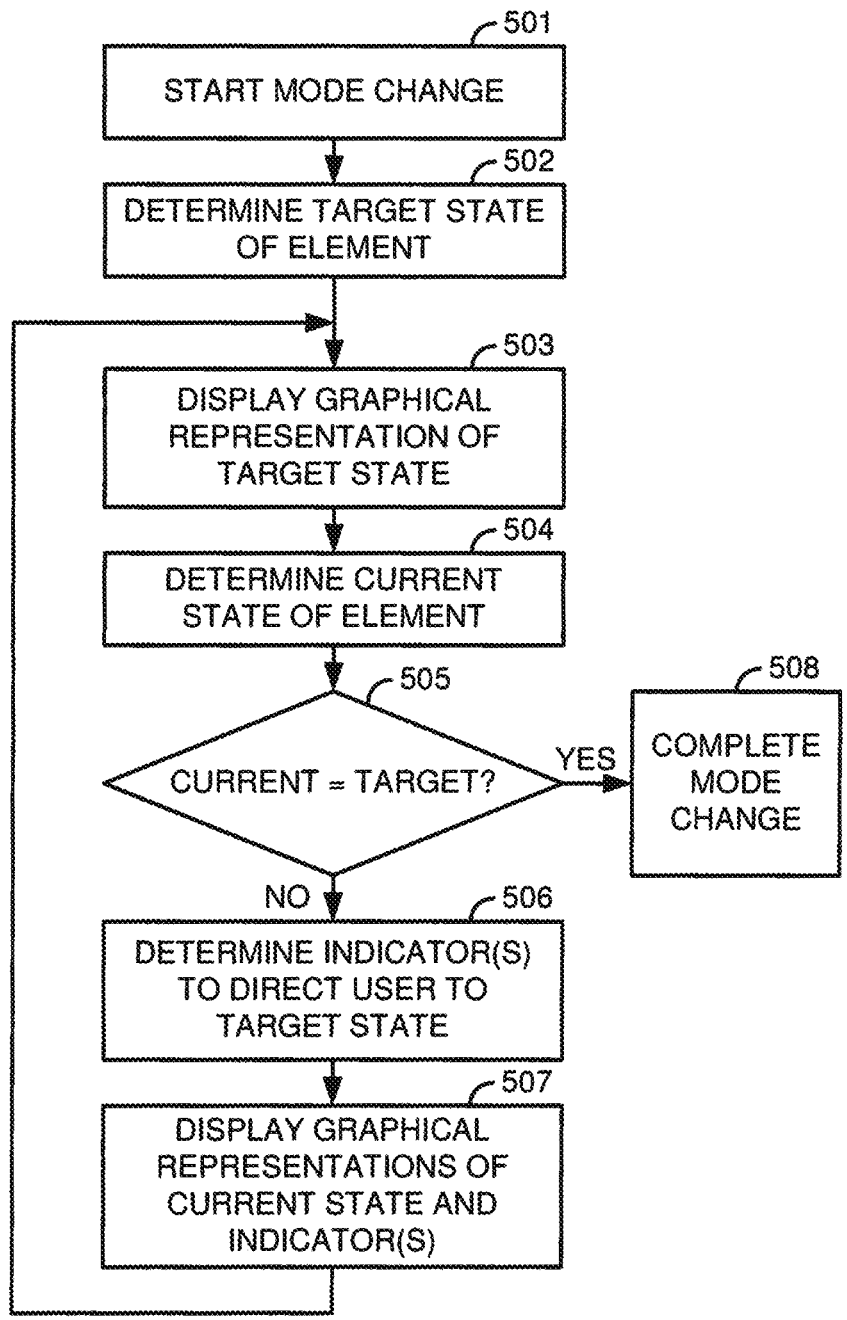
FIG. 5 illustrates a flow diagram of a method for graphically providing continuous change of state directions to a user of a medical robotic system, utilizing aspects of the present invention.

FIG. 5 illustrates a flow diagram of a method for graphically providing continuous change of state directions to a user of the medical robotic system 100 and FIGS. 6-11 illustrate several examples of graphical representations generated and displayed by the method on a display screen of the monitor 104 of the medical robotic system.

Figure 6:
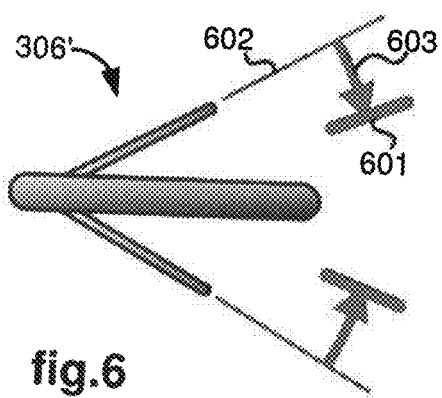
FIGS. 6-11 illustrate various examples of graphical representations displayed on a display screen for providing continuous change of state directions to a user of a medical robotic system utilizing aspects of the present invention.
Figure 7:
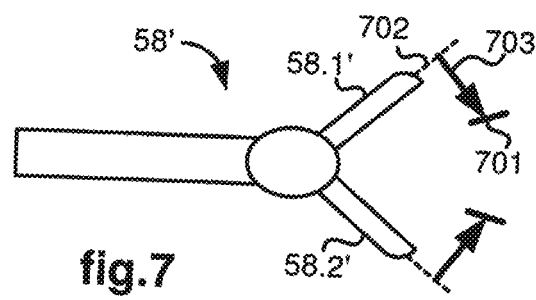
Figure 8:
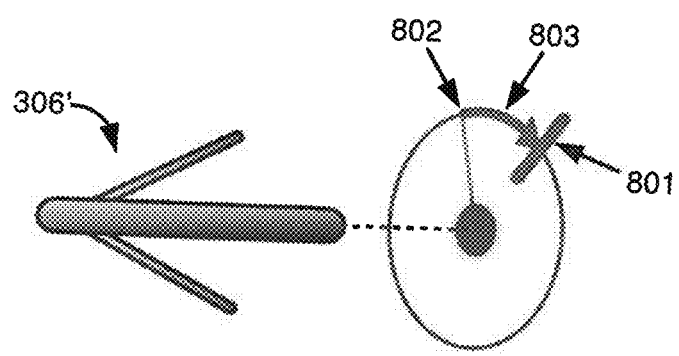
Figure 9:
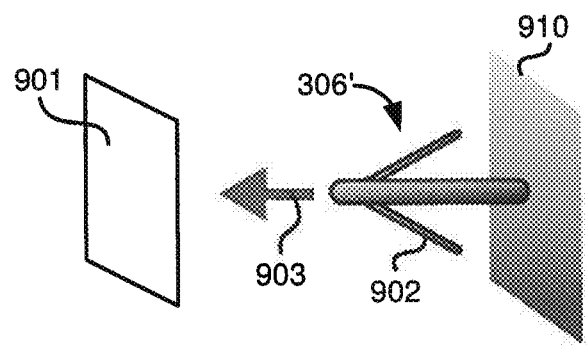
Figure 10:
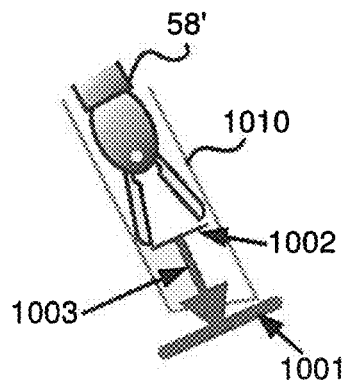
Figure 11:
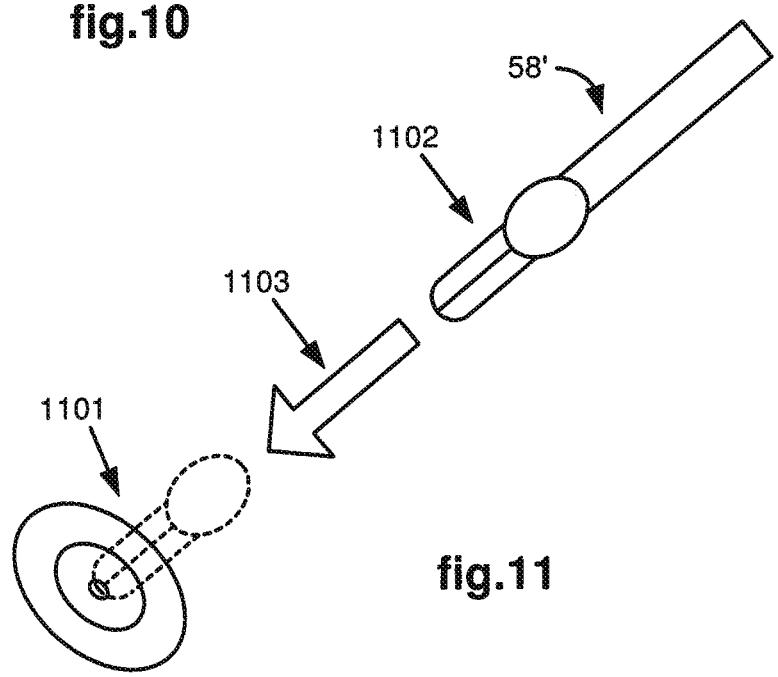

In 501, an operational mode change is initiated. One example of such a mode change is the above-described re-alignment of the input device with a surgical tool prior to re-association of the input device with the surgical tool. Examples of this type of mode change are shown in FIGS. 6-8. Another type of mode change is initiated when a joint of a slave manipulator reaches or becomes dangerously close to a limitation in its range of motion. In this case, control of the slave manipulator may be temporarily suspended (and/or a feedback force may be exerted against the input device) until the user moves the input device to a state that no longer commands exceeding the range of motion joint limit. An example of this type of mode change is shown in FIG. 9. Yet another type of mode change is initiated when a medical device is first inserted through a guide tube into a Patient. In this case, the mode change is completed when the end effector of the medical device exits the distal end of the guide tube. An example of this type of mode change is shown in FIG. 10. Still another type of mode change is a guided tool change in which a replacement tool is guided to a position formerly held by the tool which it has replaced. An example of this type of mode change is shown in FIG. 11. It is to be appreciated that the mode changes described herein are merely examples and that many other types of mode changes (and corrective actions within a mode) may also be used with the method described in reference to FIG. 5 and therefore, are contemplated as being within the full scope of various aspects of the present invention.

In 502, a target state for an element of the medical robotic system 100 is determined. The element can be any manipulatable component of the medical robotic system that is continuously manipulated by the user to perform the requisite steps for a mode change. For example, the element may be the input device and more particularly, a pincher formation of the input device or, as another example, the element may be the medical device and more particularly, an end effector of the medical device. Note that the graphical representation of the element does not necessarily have to be a depiction of the element.

The target state is generally the state of the element that is required to satisfy the mode change criteria. For example, in FIG. 6, the target state of the element (i.e., pincher formation 306) is a pincher angle indicated by stop gap 601 which corresponds to the angle of the opening of the end effector jaws of the medical device, in its soft-locked state, prior to re-association of the input device with the medical device. Note that in this example and others described herein, the graphical representation of the pincher formation 306 is identified as 306' to distinguish it from the actual pincher formation 306. As another example, in FIG. 8, the target state of the element (i.e., pincher formation 306) is a roll angle indicated by stop gap 801 which corresponds to the roll angle of the end effector of the medical device, in its soft-locked state, prior to re-association of the input device with the medical device. As another example, in FIG. 9, the target state of the element (e.g., pincher formation 306) is a position 901 which is safely away from an initial position 910 at which one or more joints of the slave manipulator of the medical device has reached its range of motion limit or come within a threshold distance away from its range of motion limit. As another example, in FIG. 10, the target state of the element (e.g., end effector 58) is an extended position of the medical device indicated by stop gap 1001 at which its end effector exits the distal end of a guide tube (e.g., a cannula) 1010 in which the medical device has been inserted for entry into the Patient. Note that in this example and others described herein, the graphical representation of the end effector 58 is identified as 58' to distinguish it from the actual end effector 58. As another example, in FIG. 11, the target state of the element (e.g., end effector 58) is the position and orientation that the replacement tool is to be moved to in order to occupy the same state that the tool which it is replacing previously occupied for performing a medical procedure at a worksite within a Patient. The target state in this example is graphically represented advantageously by a three-dimensional ghost image 1101 of the end effector so that both position and orientation may be indicated.

In 503, a graphical representation of the determined target state is displayed on the display screen 104. Typically, the graphical representation of the target state depicts the element such as shown in FIGS. 6, 8-11. However, this is not a necessary requirement of the method of FIG. 5. For example, in both FIGS. 6, 7, the same mode change is being performed in which the element is the input device and the mode change involves re-aligning the open angle of the pincher formation with the open angle of the end effector's jaws before re-associating the medical device with the input device. In FIG. 6, the graphical representation of the target state of the element depicts the pincher formation 306. However, in FIG. 7, it depicts the state of the end effector 58 which would be commanded by the pincher formation 306 if the medical device were associated with the input device at the time. Thus, the target state graphically depicted by stop bar 701 in FIG. 7 indicates a command corresponding to the held position of the end effector 58.

In 504, a current state of the element is determined. When the element is the input device (or part thereof), the determination of its current state is preferably performed using sensed joint positions of the input device and applying the sensed positions to forward kinematics of the input device. On the other hand, when the element is the medical device (or part thereof), the determination of its current state is preferably performed using sensed joint positions of the slave manipulator manipulating the medical device and applying the sensed positions to forward kinematics of the slave manipulator.

In 505, a determination is made whether the current state matches the target state (i.e., the current state of the element has reached the target state of the element).

To perform this comparison, it is useful to first determine the target state of the element in same coordinate system as the current state of the element. Although described at this point, such determination may be advantageously performed in 502 above. In the case where the target state is a held (soft-locked) position of the medical device, such as in the examples of FIGS. 6-8, the held state may be determined using sensed joint positions of the slave manipulator manipulating the medical device and applying the sensed positions to forward kinematics of the slave manipulator. In the case where the target state is determined by backing off to a safe distance from a current joint position of the slave manipulator, such as in the example of FIG. 9, the target state may be determined by first determining the current position of the device and backing off from that position by the safe distance. The current position of the device in this case may be determined using sensed joint positions of the slave manipulator manipulating the device and applying the sensed positions to forward kinematics of the slave manipulator. In the case where the target state depends on the position of another structure, such as in the guide tube example of FIG. 10, the position of the guide tube may be determined using sensed joint positions of a slave manipulator manipulating the guide tube and applying the sensed positions to forward kinematics of the slave manipulator. In the case where the target state is the former position of a replaced medical device, such as in the example of FIG. 11, the position of the medical device that is being replaced may be determined using sensed joint positions of the slave manipulator manipulating the medical device and applying the sensed positions to forward kinematics of the slave manipulator. The determined position is then stored in a non-volatile memory of the medical robotic system so that it may be used for generating the target state at a later time.

Now if the determination in 505 is YES, then in 508, the operational mode change is completed since the element has successfully reached its target state. As an example of such completion, with respect to FIGS. 6-8, the medical device is re-associated with the input device. As another example of such completion, with respect to FIG. 9, the robotic control of the medical device is re-activated since its slave manipulator is no longer in danger of reaching a range of motion limit on one of its joints.

On the other hand, if the determination in 505 is NO, then in 506, one or more indicators are determined that would direct the user to move the element towards its target state. Determination of what the indicator(s) should indicate in this case is straightforward since the current and target states are known. It is important to note, however, that the indicator(s) is/are not static. The indicator(s) may continually change as the element is manipulated by the user towards the target state. Thus, the indicator(s) is/are dynamic in this sense.

In 507, graphical representations of the current state and the one or more indicators are displayed on the display screen 104 along with the graphical representation of the target state. As examples, the current state of the pincher formation angle is indicated by arc line 602 and its corresponding indicator by arrow 603 in FIG. 6; the current state of the pincher formation angle is indicated by the commanded jaw position 702 and its corresponding indicator by arrow 703 in FIG. 7; the current state of the pincher formation roll angle is indicated by point 802 and its corresponding indicator by arrow 803 in FIG. 8; the current state of the pincher formation is indicated by a graphical representation 902 of the pincher formation and its corresponding indicator by arrow 903 in FIG. 9; the current state of the end effector is indicated by a line 1002 shown in front of a graphical representation of the end effector and its corresponding indicator by arrow 1003 in FIG. 10; and the current state of the end effector is indicated by a graphical representation 1102 of the end effector and its corresponding indicator by arrow 1103 in FIG. 11. Although each of these examples shows a graphical representation for only a single indicator, more than one indicator may be depicted at one time. For example, the pincher opening and roll angle targets of FIGS. 6, 8 may be combined into a single display along with their respective current states 602, 802 and indicators 603, 803. Thus, for each degree of freedom movement, a separate arrow indicator may be provided to indicate required movement in that degree of freedom.

The method then loops back to 503 to process sampled data values read from position sensors associated with the element for a next process cycle through 503-507 and continues looping through 503-507 until a YES determination is made in 505 and the method is completed in 508. Thus, change of state directions are graphically provided to the user on a continuous basis until the target state is reached.

Although the various aspects of the present invention have been described with respect to a preferred embodiment, it will be understood that the invention is entitled to full protection within the full scope of the appended claims. In particular, although the method of FIG. 5 describes its use for performing a mode change, it is to be appreciated that inventive aspects of the method may also be used within a mode where dynamic change of state actions are required by the user.

We claim:

1. A method for graphically providing continuous change of state directions to a user of a medical system that includes an input device which is operated by the user, an actuatable joint which is operatively coupled to the input device, and a display screen which is viewable by the user, the method comprising:

determining whether the actuatable joint would move within a threshold distance from a range of motion limitation of the actuatable joint in response to a current state of the input device; and if it is determined that the actuatable joint would move within the threshold distance from the range of motion limitation of the actuatable joint in response to the current state of the input device, then (i) displaying a graphical representation of a target state of the input device on the display screen, wherein the target state corresponds to a most recent state of the input device which did not result in the actuatable joint moving within the threshold distance from the range of motion limitation of the actuatable joint, (ii) continuously determining current states of the input device and current indications directing the user to manipulate the input device towards the target state, and (iii) displaying graphical representations of the current states of the input device and graphical representations of the current indications along with the graphical representation of the target state of the input device on the display screen.

2. The method according to claim 1, wherein the input device has a pincher formation, and wherein the displaying graphical representations of the current states of the input device on the display screen comprises:

displaying a graphical representation of the pincher formation that moves on the display screen so that a current distance between the displayed graphical representation of the pincher formation and the displayed graphical representation of the target state of the input device indicates a difference between the current state of the input device at that time and the target state of the input device.

3. The method according to claim 1, wherein the displaying graphical representations of the current indications on the display screen comprises:
displaying each graphical representation of the current indication as an arrow pointing from the displayed graphical representation of the current state of the input device to the displayed graphical representation of the target state of the input device so as to direct the user to manipulate the current state of the input device towards the target state of the input device.

4. The method according to claim 1, further comprising:
if it is determined that the actuatable joint would move within the threshold distance from the range of motion limitation of the actuatable joint in response to the current state of the input device, then providing force feedback on the input device until the current state of the input device reaches the target state of the input device.

5. The method according to claim 1, further comprising:
determining whether the actuatable joint would reach the range of motion limitation of the actuatable joint in response to the current state of the input device; and
if it is determined that the actuatable joint would reach the range of motion limitation of the actuatable joint in response to the current state of the input device, then suspending operative coupling between the input device and the actuatable joint, so that the actuatable joint does not move in response to the current state of the input device.

6. A medical system comprising:
a slave manipulator having a plurality of actuatable joints;
an input device operatively coupled to the plurality of actuatable joints;
a display screen viewable by a user of the medical system; and
a processor programmed to:
determine whether an actuatable joint of the plurality of actuatable joints would move within a threshold distance from a range of motion limitation of the actuatable joint in response to a current state of the input device; and
if it is determined that the actuatable joint would move within the threshold distance from the range of motion limitation of the actuatable joint in response to the current state of the input device, then
(i) cause a graphical representation of a target state of the input device to be displayed on the display screen, wherein the target state corresponds to a most recent state of the input device which did not result in the actuatable joint moving within the threshold distance from the range of motion limitation of the actuatable joint,
(ii) continuously determine current states of the input device and current indications directing the user to manipulate the input device towards the target state; and
(iii) cause graphical representations of the current states of the input device and graphical representations of the current indications to be displayed along with the graphical representation of the target state on the display screen.

7. The medical system according to claim 6, wherein the input device has a pincher formation, and wherein the processor is programmed to cause the graphical representations of the current states of the input device to be displayed on the display screen by causing a graphical representation of the pincher formation to move on the display screen so that a current distance between the displayed graphical representation of the pincher formation and the displayed graphical representation of the target state of the input device distance indicates a difference between the current state of the input device at that time and the target state of the input device.

8. The medical system according to claim 6, wherein the processor is programmed to cause graphical representations of the current indications to be displayed on the display screen by causing each graphical representation of the current indication to be displayed as an arrow pointing from the displayed graphical representation of the current state of the input device to the displayed graphical representation of the target state of the input device so as to direct the user to manipulate the current state of the input device towards the target state of the input device.

9. The medical system according to claim 6, wherein the processor is programmed to:
if it is determined that the actuatable joint would move within the threshold distance of the range of motion limitation of the actuatable joint in response to the current state of the input device, then command force feedback on the input device until the current state of the input device reaches the target state of the input device.

10. The medical system according to claim 6, wherein the processor is programmed to:
determine whether the actuatable joint of the plurality of actuatable joints would reach the range of motion limitation of the actuatable joint in response to the current state of the input device; and
if it is determined that the actuatable joint would reach the range of motion limitation of the actuatable joint in response to the current state of the input device, then suspend operative coupling between the input device and the plurality of actuatable joints, so that the plurality of actuatable joints do not move in response to the current state of the input device.

\* \* \* \* \*